United States Patent
Wind et al.

[11] Patent Number: 5,804,703
[45] Date of Patent: Sep. 8, 1998

[54] CIRCUIT FOR A COMBUSTIBLE GAS SENSOR

[75] Inventors: Robert Harold Wind, Grand Blanc; Paul Charles Spagnuolo, Owosso, both of Mich.

[73] Assignee: General Motors Corporation, Detroit, Mich.

[21] Appl. No.: 871,137

[22] Filed: Jun. 9, 1997

[51] Int. Cl.[6] .............................. G01N 27/16; G01M 3/25
[52] U.S. Cl. .................... 73/25.01; 73/23.31; 422/94; 324/648; 324/706
[58] Field of Search ............................. 73/25.01, 23.31, 73/23.32; 422/94; 324/706, 648

[56] References Cited

U.S. PATENT DOCUMENTS

| | | | |
|---|---|---|---|
| 1,880,941 | 10/1932 | Erickson | 73/27 |
| 2,404,993 | 7/1946 | Sullivan | 23/255 |
| 2,720,108 | 10/1955 | Johnson | 73/27 |
| 3,069,896 | 12/1962 | Kindred et al. | 73/23 |
| 3,138,436 | 6/1964 | Harmon | 23/253 |
| 3,153,577 | 10/1964 | McCully et al. | 23/255 |
| 3,188,553 | 6/1965 | Eurenius | 323/69 |
| 3,237,181 | 2/1966 | Palmer | 340/237 |
| 3,251,654 | 5/1966 | Palmer | 23/255 |
| 3,347,635 | 10/1967 | McKee | 23/232 |
| 3,687,631 | 8/1972 | Zegel | 23/232 |
| 3,753,369 | 8/1973 | Fowler et al. | 73/15.4 |
| 4,036,592 | 7/1977 | Brown et al. | 23/232 E |
| 4,314,475 | 2/1982 | Karpov et al. | 73/27 R |
| 4,317,796 | 3/1982 | Barr | 422/95 |
| 4,870,025 | 9/1989 | Hurley et al. | 436/141 |
| 5,360,266 | 11/1994 | Lenfers et al. | 374/36 |
| 5,410,908 | 5/1995 | Erichsen | 73/31.05 |
| 5,428,985 | 7/1995 | Kurtz et al. | 73/25.01 |
| 5,473,304 | 12/1995 | Friese et al. | 338/23 |
| 5,549,871 | 8/1996 | Kocache et al. | 422/95 |

*Primary Examiner*—Hezron E. Williams
*Assistant Examiner*—J. David Wiggins
*Attorney, Agent, or Firm*—Anthony Luke Simon

[57] ABSTRACT

A circuit for a combustible gas sensor comprising: a bridge circuit having first and second legs; a first node at a first midpoint in the first leg of the bridge circuit; a second node at a second midpoint in the second leg of the bridge circuit; a first temperature responsive resistive sensor element coupled between the first node and a bottom of the bridge circuit and located in a flow of combustible gas; a second temperature responsive resistive sensor element coupled between the bottom of the bridge and ground and located in the flow of combustible gas; and a voltage control circuit coupled to the first and second nodes and to the top of the bridge circuit for maintaining closed loop control of first and second node voltages at the first and second nodes by varying a bridge voltage at the top of the bridge circuit wherein one of the first and second sensor elements includes a catalyst for stimulating reactions of reactive constituents in the flow of combustible gas.

2 Claims, 2 Drawing Sheets

CIRCUIT FOR A COMBUSTIBLE GAS SENSOR

This invention relates to a circuit for a combustible gas sensor.

BACKGROUND OF THE INVENTION

It is known to measure oxygen content of an internal combustion engine exhaust gas to determine whether the exhaust gas is fuel-rich, fuel lean or approximately at stoichiometry. Feedback from the exhaust gas oxygen sensor may be used to control the vehicle engine in a closed loop manner to minimize rich and/or lean excursions of the internal combustion engine exhaust gas.

It is known to use a calorimetric sensor to monitor the presence of combustible gases. One known type of calorimetric sensor uses a catalyst in proximity to a sensor, such as a thermistor, capable of measuring the temperature of the catalyst. When a mixture of reactive gases contacts the catalyst, the catalyst stimulates gas reactions that may be exothermic or endothermic. Whether the reaction is exothermic or endothermic, the reaction causes at the catalyst temperature variation as sensed by the thermistor located in proximity to the catalyst.

SUMMARY OF THE INVENTION

It is an object of this invention to provide a circuit for a combustible gas sensor in accordance with claim 1.

Advantageously, this invention provides, for a combustible gas sensor, a circuit generating electrical signals indicating the presence of and amounts of mixtures of combustible gases.

Advantageously, this invention provides a circuit for combustible gas sensor suitable for sensing unburned gas components in an internal combustion engine exhaust stream.

Advantageously, this invention provides, for a combustible gas sensor, a circuit that makes use of two temperature-responsive variable resistive sensor elements mounted in a flow stream of internal combustion engine exhaust gases. The two sensor elements are connected in a unique circuit arrangement in which one of the sensor elements is mounted in a bridge circuit having first and second legs. The first leg of the bridge circuit includes the one sensor element and a fixed resistive element and the second leg of the bridge circuit includes fixed resistive elements not placed in the flow-of exhaust gas. The other sensor element is coupled between the base of the bridge circuit and one node of the circuit power supply. The bridge circuit is controlled so that the voltages at the mid points of each leg are maintained equal. One of the sensor elements is located in proximity to a catalyst capable 27 of stimulating reaction in the gases in the flow stream. The configuration allows closed loop feedback of the voltages at the midpoint of each leg, which feedback is applied to control the voltage at the top of the bridge. The circuit also compensates for variations in mass flow of the gases flowing past the sensor elements.

Advantageously then, according to a preferred example, this invention provides a circuit for a combustible gas sensor comprising a bridge circuit having first and second legs; a first node at a first midpoint in the first leg of the bridge circuit; a second node at a second midpoint in the second leg of the bridge circuit; a first temperature responsive resistive sensor element coupled between the first node and a bottom of the bridge circuit and located in a flow of combustible gas; a second temperature responsive resistive sensor element coupled between the bottom of the bridge and a power supply line (e.g., ground) and located in the flow of combustible gas; and a voltage control circuit coupled to the first and second nodes and to the top of the bridge circuit for maintaining closed loop control of first and second node voltages by varying a bridge voltage at the top of the bridge circuit wherein one of the first and second sensor elements includes a catalyst for stimulating reactions of reactive constituents in the flow of combustible gas.

BRIEF DESCRIPTION OF THE DRAWINGS

The present invention will now be described by way of example with reference to the following drawings in which.

DETAILED DESCRIPTION OF THE INVENTION

Figure 1:
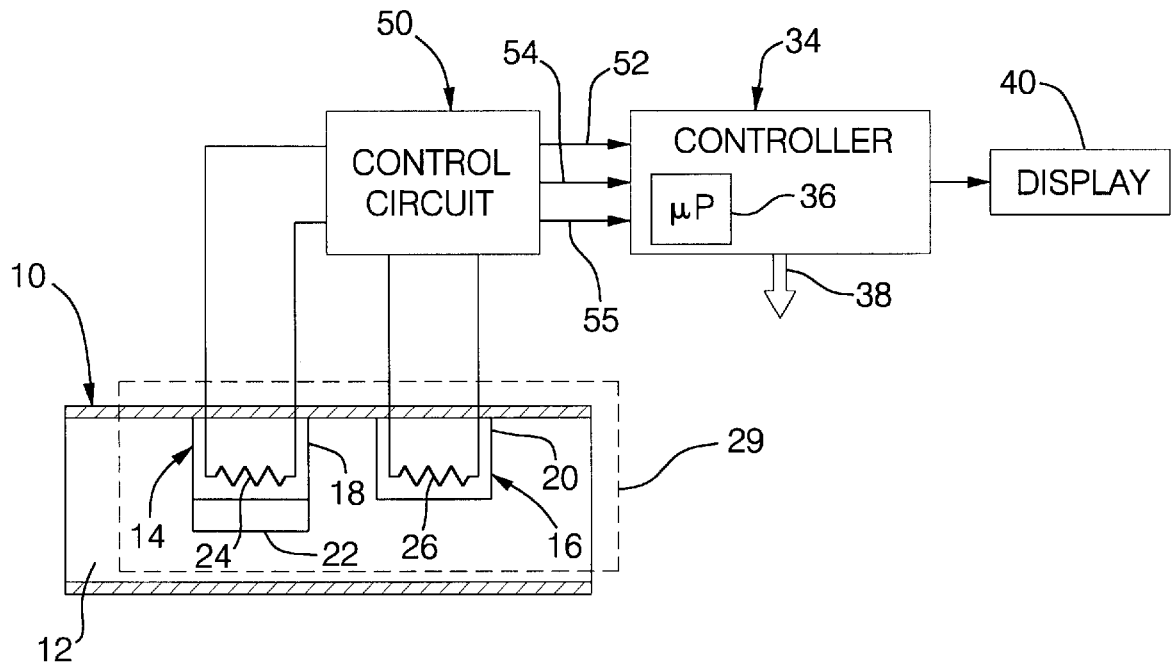
FIG. 1 is a schematic illustration of the present invention.

Referring now to FIG. 1, sensor 29 comprises first and second sensor units 14 and 16 mounted within a structure 10 defining a flow passage 12 through which the gases to be analyzed flow. Each of the sensor units 14 and 16 include a carrier 18 and 20, respectively. Carrier 18 has a temperature responsive resistive sensor element 24 mounted thereon and carrier 20 has a temperature responsive resistive sensor element 26 mounted thereon. In one example, the carriers 18 and 20 are made of ceramic, glass or other suitable material durable in a high temperature environment and the sensor elements 24, 26 are printed or deposited platinum resistors applied to the carriers 18, 20 in a known manner.

The sensor unit 14 also includes a layer of a catalyst 22 located in proximity to sensor element 24 so that the temperature of sensor element 24 is affected by the temperature of catalyst 22. The catalyst 22 is a material capable of stimulating reaction in the mixture of gases flowing through flow passage 12. For example, when flow passage 12 is in the exhaust path of an internal combustion engine, catalyst 22 may be any noble metal or other material such as platinum, palladium, rhodium, etc. or combinations of such materials capable of stimulating reactions between unburned or partially burnt hydrocarbons and oxygen in the engine exhaust gases.

The sensor units 14 and 16 may be mounted within the flow passage 12 in any suitable manner and it is understood that the sensor units 14 and 16 may be mounted on separate carriers 18 and 20 as shown or the carriers 18 and 20 may be part of a single unit including both sensor elements 24 and 26 as long as one of the sensor elements 24 and 26 is located proximate to the catalyst 22 and has its temperature influenced by the temperature of the catalyst 22.

More particularly, when a gas mixture flows through passage 12 and impinges on catalyst material 22, the catalyst material 22 stimulates reactions between reactive constituents of the gas mixture. When the gas mixture is engine exhaust, the reactions are typically exothermic. Other gas mixtures may have endothermic reactions. In either case, the reactions cause a temperature change of the catalyst 22, which by virtue of its proximity to sensor element 24, affects the temperature of sensor element 24 and therefore affects the impedance of sensor element 24. The amount of temperature change of the catalyst 22 and thereby of the sensor element 24 depends upon the amount of reactive constituents within the exhaust gases flowing through the passage 12.

The control circuit 50 monitors the resistances of sensor elements 24 and 26 and the relationship between the two resistances. Control circuit 50 provides output signals on lines 52, 54 and 55 indicative of the amount of variance of resistance of sensor element 24 compared to that of sensor element 26. The output signals are provided to controller 34 having an internal microprocessor 36 and standard circuits for interfacing the signals on lines 52, 54 and 55 to the microprocessor 36 in a known manner. Output interface circuits of a known type (not shown) provide output signals, for example, through bus 38 to provide the exhaust gas content information to another controller that executes, for example, closed loop engine control commands to achieve desired fuel control in a known manner responsive to the exhaust gas content as determined by the signals output from circuit 50.

Additionally, a signal may be provided to a display 40 to indicate when a certain condition, for example, too many reactive constituents of the gases flowing through passage 12, occurs. Alternatively, when the circuit 30 and controller 34 are used in test equipment, the signal indicates a measure of reactive constituents of gases flowing through passage 12.

During operation, control circuit 50 controls the voltage and/or current to the sensor elements 24 and 26 to achieve the desired operation of the sensor 29.

Figure 2:
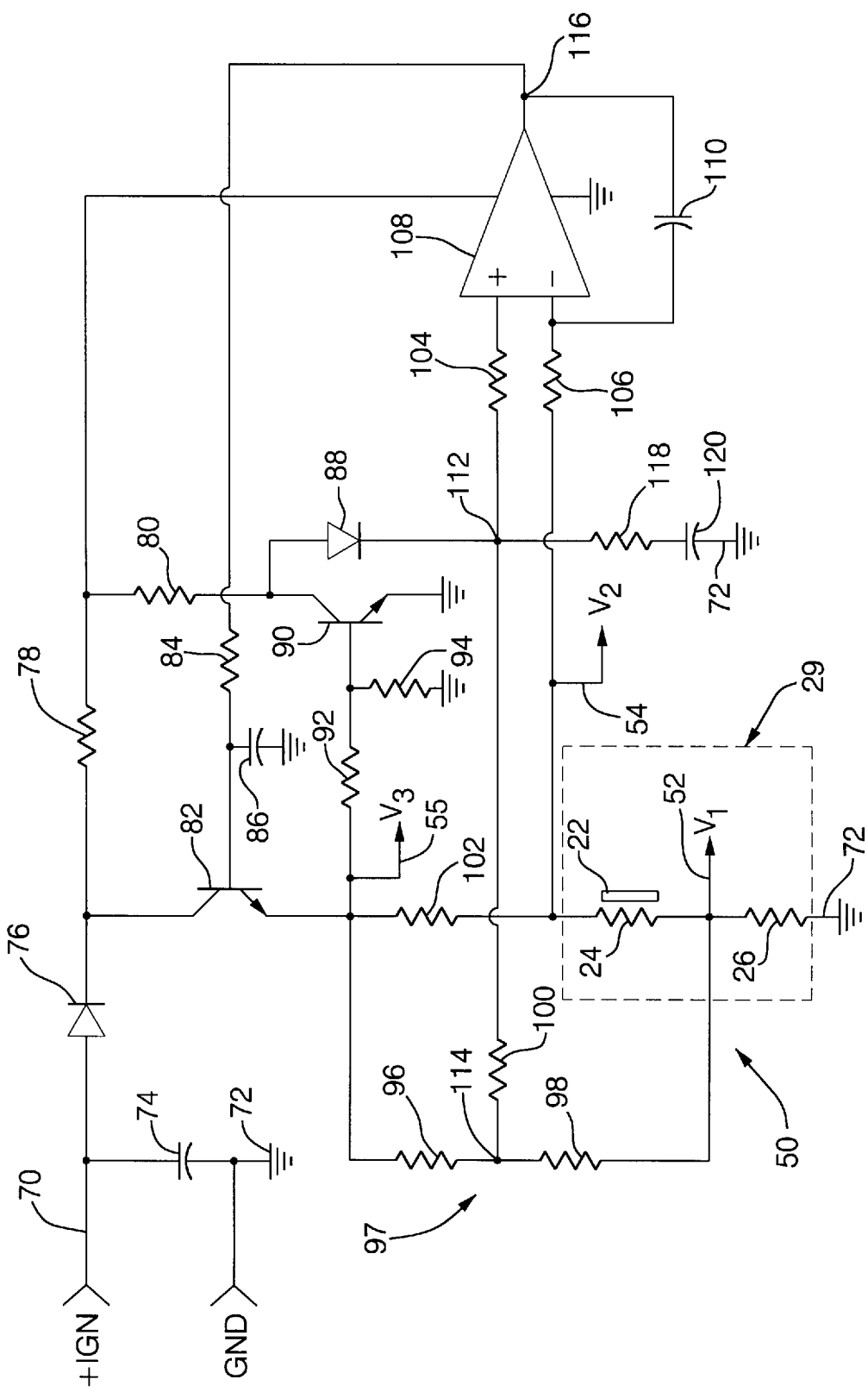
FIG. 2 illustrates an example sensor control circuit 50 of FIG. 1.

Referring now to FIG. 2, an example implementation of the sensor control circuit 50 is shown. The example sensor control circuit 50 includes a bridge 97 having a upper voltage node 55 and a lower voltage node 52. A first leg is connected between the upper and lower voltage nodes 55 and 52 and comprising resistors 96 and 98 connected in series at node 114. A second leg of the bridge circuit is formed between upper and lower voltage nodes 55 and 52 comprising resistor 102 and sensor element 24 connected in series at node 54. Power is provided to the bridge 97 through node 55 from Darlington transistor 82 having its emitter connected to node 55 and its collector connected to diode 76.

Diode 76 receives power from high voltage line 70, which is stabilized by capacitor 74 connected between line 70 and ground 72. In an example where the circuit is used in the motor vehicle, line 70 represents the ignition power voltage line for the vehicle.

The base of transistor 82 is coupled via resistor 84 and capacitor 86 to the output 116 of amplifier 108, as shown, whose function will be described further below.

At the low voltage node 52 of the bridge 97, sensor element 26 is connected between node 52 and ground. In the bridge, resistors 96 and 98 are provided with impedances much higher (e.g., at least ten times higher) than those of resistor 102 and sensor element 24 so that virtually all of the current through the bridge 97 flows through resistor 102 and sensor element 24. In the case where resistors 96 and 98 are sized so that they receive less than ten percent (more ideally, on the order of one percent or less) of the current through resistor 102 and sensor element 24, then the current through sensor elements 24 and 26 can be approximated as equal.

During normal operation, the sensor control circuit 50 controls current through sensor element 24 to maintain the temperature of sensor element 24 above the light off temperature of the catalyst 22 in proximity to sensor element 24. The resistors 96, 98 and 102 are calibrated so that, during normal operation, the voltages at nodes 114 and 54 are equal or, alternatively, at predetermined relative levels.

Resistors 100, 104 and 106, all having relatively low impedances, couple the nodes 114 and 54 to the inputs of operational amplifier 108. The output 116 of operational amplifier 108 varies, increasing as the voltage of node 114 rises above the voltage of node 54 and decreasing as the voltage of node 114 falls below the voltage of node 54. The output 116 is coupled through resistor 84 to the base of transistor 82, which controls the voltage of node 55, thus providing closed loop feedback control of the voltage at node 55, adjusting the voltage to maintain the voltages of nodes 114 and 54 at the target level and, in the process, also maintaining the resistance of resistor 24 at a fixed ratio to the resistance of resistor 102.

When, through catalytic operation, reactive constituents of gases react at the location of catalyst 22, creating an exothermic or endothermic result, catalyst 22 changes temperature and, by its close proximity to sensor element 24, changes the temperature and therefore the resistance of sensor element 24. The amount of current flow through sensor element 24 is relational to the resistance of sensor element 24. Thus, as the temperature of sensor element 24 changes due to operation of the catalyst causing reactions of the gas constituents, the value of the resistance of sensor element 24 changes, which directly affects the voltage at node 54 in the midpoint of one leg of the bridge circuit 98. When the voltage at node 54 changes, the output of amplifier 108 on line 116 changes, changing the supply voltage through transistor 82 to the bridge 97 until the nodes 114 and 54 are equalized again.

Resistor 118 and capacitor 120 attenuate high frequency feedback components that may tend to otherwise cause the closed loop control circuit to oscillate.

Assuming that sensor elements 24 and 26 are substantially matched thermally responsive resistors, the difference in temperature between sensor element 24 and sensor element 26 is directly relational to the difference in voltage drops across sensor element 24 and sensor element 26. Restated, the difference in temperature between sensor elements 24 and 26 due to activity of the catalyst 22 is directly relational to $V_2-2*V_1$, where $V_2$ is the voltage at node 54 and $V_1$ is the voltage at node 52.

If the sensor elements 24 and 26 are placed in the passage where substantial mass flow of gas passes by the sensors, the mass flow of gas can have a cooling effect on the sensor elements, causing control circuit 50 to vary the amount of current supplied to the sensor elements 24 and 26 to keep the bridge 97 operating at the calibrated range. To eliminate mass flow variations, the current through the sensor elements 24 and 26, which may be approximated as equal due to the higher impedances of resistors 96 and 98 compared to those of resistors 102 and sensor element 24, is eliminated as a factor by dividing the above equation, $V_2-2*V_1$ by the current through sensor element 26. The current through sensor element 26 can be represented by $I=(V_3-V_2)/R$, where $V_3$ is the voltage at node 55 at the top of the bridge 97 and R is the resistance of resistor 102. Thus a representation of percentage of reactive gas constituents to which sensor elements 24 and 26 are exposed may be achieved by dividing $V_2-2*V_1$ by I, defined above.

In an alternative method to compensating for mass air flow effect, mass air flow can be measured directly with a mass air flow sensor and a compensation function can be calibrated in a test circuit and programmed into a look-up table. For example, the look up table may have inputs being $V_2-2*V_1$ and the measured mass flow and the output being the correct measure of reactive gas constituents, for example, as measured by a calibrating sensor.

Transistor 90 is included as a part of a start-up circuit within sensor control circuit 50. When line 70 is first powered up, i.e., when the vehicle ignition is started, power flows through resistors 78 and 80 to transistor 90 and through diode 88 to node 112 coupled to the input of amplifier 108 through resistor 104. In response to the power-up of line 70, node 112 goes high forcing output 116 of amplifier 108 high, driving transistor 82 on. When transistor 82 is turned on, current flowing through the bridge 97 forces the voltage at node 55 to rise. Node 55 is coupled to the base of transistor 90 via resistors 92 and 94. Thus, as the voltage of node 55 rises, transistor 90 turns on. When the voltage at node 55 rises sufficiently enough that transistor 90 becomes saturated, the collector voltage of transistor 90 lowers to approximately 0.1 volts above ground. When the voltage at the collector of transistor 90 is lower than that at node 112, diode 88 isolates node 112 from the transistor 90 so that transistor 90 no longer has influence on the inputs to amplifier 108 and amplifier 108 responds solely to the voltages at nodes 114 and 54 to provide closed loop control to the bridge circuit 97 as described above.

Figure 3:
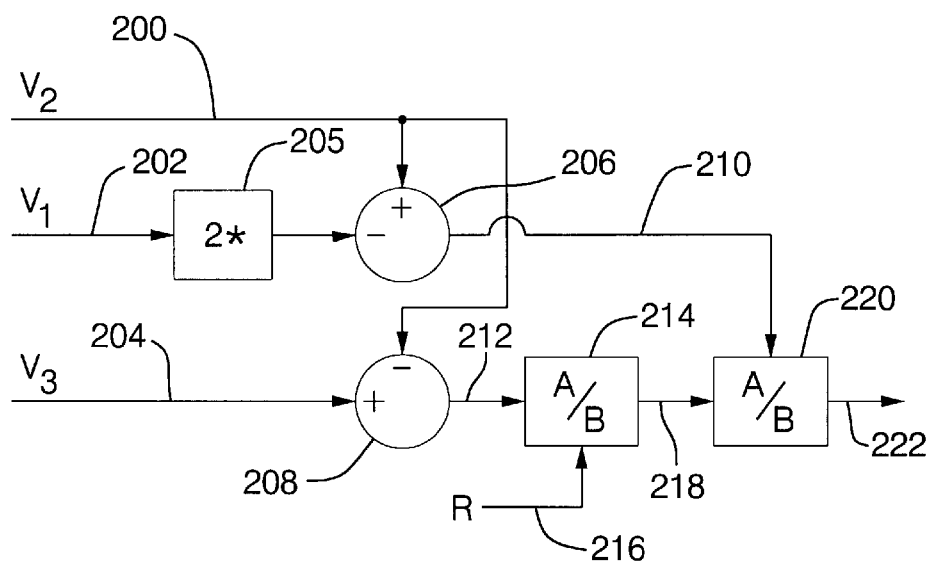
FIG. 3 illustrates example operation of controller 34 of FIG.

Referring now to FIG. 3, an example implementation of the functions performed by the microprocessor 36 within controller 34 is shown. The signals $V_1$, $V_2$ and $V_3$, after being input via the microprocessor's internal analog to digital converter (not shown), are provided as digital signals as represented by lines 200, 202 and 204. $V_1$ is multiplied by a factor of two, as represented by block 205 and then subtracted from $V_2$, as represented by block 206. The result is the quantity $V_2-2*V_1$, represented by line 210.

The signal $V_2$ is subtracted from $V_3$ as represented by block 208 and the result, represented by line 212, is divided by the value R (line 216, the resistance of resistor 102) as represented by block 214. The result of the division function block 214 is the current through sensor element 24 and represented by line 218, which is divided from the signal represented by line 210, as represented by block 220. The resultant signal represented by line 222 represents the amount of reactive constituents of gases to which sensor 29 is exposed.

In an alternative example implementation, the catalyst 22 is placed near sensor element 26 while no catalyst is placed near sensor element 24. In this example, resistor 98 can be made temperature sensitive and placed in the gas stream to compensate for temperature variations of the gas stream on the sensor 29 and on the outputs of circuit 50. Alternatively, temperature can be measured directly by a known type of temperature sensor and provided as an input to microprocessor 36, which then includes a function (e.g., a look-up table) for compensating the output signal 222 (FIG. 3) as a function of temperature. Similarly, a signal representing mass flow of gas past the sensor 29 can be provided to the microprocessor 36 and a similar look-up table compensation function can be applied to compensate output signal 222 for variations due to changes in mass flow of gas past sensor 29. The look-up table functions can be calibrated by one skilled in the art using a test set up of the system shown in FIG. 1 and an alternative sensing means for sensing reactive gas constituents. The output of the alternative sensing means is used to calibrate the look-up table outputs with the inputs provided by signal 222, temperature and mass flow.

The invention claimed is:

1. A circuit for a combustible gas sensor comprising:

a bridge circuit having first and second legs;

a first node at a first midpoint in the first leg of the bridge circuit;

a second node at a second midpoint in the second leg of the bridge circuit;

a first temperature responsive resistive sensor element coupled between the first node and a bottom of the bridge circuit and located in a flow of combustible gas;

a second temperature responsive resistive sensor element coupled between the bottom of the bridge circuit and a power supply line and located in the flow of combustible gas; and a voltage control circuit coupled to the first and second nodes and to the top of the bridge circuit for maintaining closed loop feedback control of first and second node voltages at the first and second nodes by varying a bridge voltage at the top of the bridge circuit wherein one of the first and second sensor elements includes a catalyst for stimulating reactions of reactive constituents in the flow of combustible gas, wherein the first leg of the bridge circuit comprises the first sensor element and a first resistor; and the second leg of the bridge circuit comprises second and third resistors, wherein the second and third resistors have second impedances much higher than first impedances of the first resistor and first sensor element, wherein current through the first and second sensor elements is maintained substantially equal at all times.

2. A circuit for a combustible gas sensor according to claim 1, wherein the catalyst is located proximate to the first sensor element wherein a first temperature and a resistance of the first sensor element are responsive to a second temperature of the catalyst.

* * * * *